United States Patent [19]

Kanemura et al.

[11] Patent Number: 5,374,668
[45] Date of Patent: Dec. 20, 1994

[54] CASTING EPOXY RESIN, POLYTHIOL AND RELEASING AGENT TO FORM LENS

[75] Inventors: Yoshinobu Kanemura; Katsuyoshi Sasagawa; Masao Imai, all of Yokohama, Japan

[73] Assignee: Mitsui Toatsu Chemicals, Inc., Tokyo, Japan

[21] Appl. No.: 150,536

[22] PCT Filed: May 1, 1989

[86] PCT No.: PCT/JP89/00454
§ 371 Date: Dec. 11, 1989
§ 102(e) Date: Dec. 11, 1989

[87] PCT Pub. No.: WO89/10575
PCT Pub. Date: Nov. 2, 1989

Related U.S. Application Data

[63] Continuation of Ser. No. 821,870, Jan. 16, 1992, abandoned, which is a continuation of Ser. No. 445,662, Dec. 11, 1989, abandoned.

[30] Foreign Application Priority Data

Apr. 30, 1988 [JP] Japan ............... 63-105466

[51] Int. Cl.$^5$ ................ C08K 5/06; C08K 5/19; C08K 5/53; C08K 5/54
[52] U.S. Cl. ................ 523/451; 359/642; 523/455; 523/456; 523/461; 523/465
[58] Field of Search .......... 523/451, 455, 456, 461, 523/463

[56] References Cited

U.S. PATENT DOCUMENTS

| | | | |
|---|---|---|---|
| 2,789,958 | 4/1957 | Fettes et al. | 525/523 |
| 3,848,612 | 11/1974 | Vogel et al. | 528/360 |
| 3,947,522 | 3/1976 | Shelley, Jr. et al. | 525/115 |
| 4,383,090 | 5/1983 | Slocki et al. | 525/502 |
| 4,594,291 | 6/1986 | Bettram et al. | 525/485 |
| 4,734,475 | 3/1988 | Goldenberg et al. | 525/326.5 |
| 4,788,233 | 11/1988 | Sakakibara et al. | 523/451 |
| 4,818,801 | 4/1989 | Rice et al. | 526/246 |
| 4,868,229 | 9/1989 | Hart | 523/400 |
| 4,975,328 | 12/1990 | Hirose et al. | 523/106 |

FOREIGN PATENT DOCUMENTS

171198  2/1986  European Pat. Off. .
2086909  5/1982  United Kingdom .

OTHER PUBLICATIONS

Patent Abstracts of Japan, vol. 13, No. 313 (C-6189)[3661], Jul. 17, 1989 (JPA 198615).

*Primary Examiner*—Robert E. Sellers
*Attorney, Agent, or Firm*—Burns, Doane, Swecker & Mathis

[57] ABSTRACT

The present invention relates to a polysulfide based resin lens, comprising a mixture of at least one epoxy resin having at least two epoxy groups, and at least one polythiol compound having at least two mercaptan groups, and at least one internal release agent, which is cast polymerized, and the process for preparing the same.

6 Claims, No Drawings

CASTING EPOXY RESIN, POLYTHIOL AND RELEASING AGENT TO FORM LENS

This application is a continuation, of application Ser. No. 07/821,870, filed Jan. 16, 1992, now abandoned, which is a continuation of application Ser. No. 07/445,662, filed on Dec. 1, 1989, now abandoned.

BACKGROUND OF THE INVENTION

1. Field of the Invention

The present invention relates to a polysulfide based resin lens, comprising a mixture of at least one epoxy and/or episulfide resin (hereinafter referred to as epoxy resin) having at least two epoxy groups and/or episulfide groups, and at least one polythiol compound having at least two mercapto groups and at least one internal releasing agent, which is cast, polymerized, and the process for preparing the same. Plastic lenses are lightweight, less fragile than inorganic lenses and can be dyed with ease.

2. Description of the Prior Art

A resin currently widely used in lenses is a radical polymerization product of diethylene glycol bisallyl carbonate (hereinafter referred to as DAC). The resin has excellent impact resistance, is lightweight, has prominent dye-affinity and good machinability including cutting ability and polishing ability.

However, lenses prepared from the resin have a smaller refractive index ($n_D=1.50$) than inorganic lenses ($n_D=1.52$). In order to obtain equivalent optical properties as glass lenses, it is necessary to increase the center thickness, peripheral thickness and curvature of the lens and hence the lens as a whole becomes inevitably thick. Therefore, resins providing a higher refractive index are desired.

Other resins which have been proposed to provide high refractive indices include resins obtained by reacting an epoxy resin with acrylic acid or methacrylic acid and subsequently radical polymerizing the resultant epoxy (meth)acrylate compound (Japanese Pat. Laid-Open No. 164607/1983), resins obtained by curing an epoxy resin with acid anhydride (Japanese Pat. Laid-Open No. 164618/1983 and 22001/1984), resins obtained by curing an epoxy resin with acid anhydride in admixture with a vinyl monomer (Japanese Pat. Laid-Open No. 164617/1983), resins obtained by curing an epoxy resin with an aromatic compound having phenolic hydroxyl groups (Japanese Pat. Laid-Open No. 24201/1988); and resins obtained by copolymerizing epoxy resins with each other (Japanese Pat. Laid-Open No. 93720/1984).

No prior art, however, has been known on the preparation of lens by curing epoxy resins with polythiol compounds.

On the other hand, plastic lenses are a rigid body completely free from bubbles that is required to have a high surface accuracy, such an optical homogeneity that any strain cannot be found by an optical strain meter, and high transparency. Generally, as a method of making plastic lenses, use is made of cutting and abrading, hot press molding, cast molding, injection molding or the like, and when a thermosetting resin such as DAC is used as a material, cast molding is used. In this case, the releasability between the lens and the mold is important, and if the release is premature, the lens surface is disturbed, or the lens is liable to be strained, whereas if the release becomes difficult, exfoliation of the mold takes place. Although it is known that butyl phosphate is used as a releasing agent for DAC, generally it is not preferable to use an internal releasing agent in view of the physical properties of the lens (see "Polymer Digest" by Seiichi Miuma, 3, 39 (1984), etc.).

However, generally when an epoxy resin based lens is cast, the adhesion between the lens and the mold is so good that the lens cannot be released from the mold easily.

However, although lenses prepared from the preceding resins have higher refractive indices than lenses prepared from DAC, the lenses do not exhibit the desired high refractive indices. Further, since such resins are prepared from compounds containing many halogen atoms or aromatic rings to improve the refractive index, lenses prepared from these resins have disadvantages such as large dispersion of refractive index, poor weatherability and high specific gravity.

On the other hand, as a method of improving the releasability for casting epoxy resin based lenses, we have tried a method of treating the mold with an external releasing agent and a method that uses a mold of a polyolefin resin.

However, the method wherein a fluorine type external releasing agent or a silicon type external agent is used to form a release film on the mold was accompanied by such problems that the thickness of the release film was difficult to become constant, part or all of the release film was transferred to the surface of the polymerized lens or into the inside of the polymerized lens which caused deterioration of the surface, and more specifically the surface was made non-uniform or the lens became turbid. In addition, because it was required to treat the mold with a releasing agent every time when the mold was used repeatedly, it was found that the method was troublesome as an industrial lens molding method, the productivity of the lens by the method was low, and the method was quite uneconomical.

On the other hand, in the method that uses a mold of a polyolefin resin, because a high temperature deforms the resin mold, the surface accuracy of the molded lens was poor, and it was found that, in the field of optical lenses and lenses for glasses wherein a high surface accuracy is required, an improvement in the method was required.

SUMMARY OF THE INVENTION

The inventors have studied to find that a polysulfide based resin lens, comprising a mixture of epoxy resin and polythiol compound and an internal releasing agent, which is cast polymerized can provide excellent opticophysical properties and a high surface accuracy without a special surface treatment of the glass that is generally used as a mold, leading to the present invention.

That is, the present invention relates to a polysulfide based resin lens, comprising a mixture of at least one epoxy and/or episulfide resin having at least two epoxy groups and/or episulfide groups, and at least one polythiol compound having at least two mercapto groups, and at least one internal releasing agent, which is casted, and the process for preparing the same.

DETAILED DESCRIPTION OF THE INVENTION

Reference will now be in detail to the present preferred embodiments of the invention.

Exemplary epoxy resins suitable for use in the practice of this invention include:

(i) Amine based epoxy resin

Amine based epoxy resins contain a group of the formula

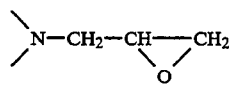

and include, for example, resins prepared by reacting compounds having amino groups and/or amide groups such as N,N,N',N'-tetraglycidyldiaminodiphenylmethane, m-N,N-diglycidylaminophenylglycidyl ether and N,N,N',N'-tetraglycidylterephthalamide, with epihalohydrins such as epichlorohydrin, methylepichlorohydrin and epibromohydrin.

Exemplary suitable compounds having amino groups include diaminodiphenylmethane, m-xylylenediamine, p-xylylenediamine, m-aminobenzylamine, p-aminobenzylamine, 1,3-bis(aminomethyl)cyclohexane, 1,4-bis(aminomethyl)cyclohexane, 1,3-diaminocyclohexane, 1,4-diaminocyclohexane, m-phenylenediamine, p-phenylenediamine, benzylamine, diaminodiphenyl sulfone, diaminodiphenyl ether, diaminodiphenyl sulfide, diaminodiphenyl ketone, naphthalenediamine, aniline, toluidine, m-aminophenol, p-aminophenol and aminonaphthol.

Exemplary suitable compounds having amide groups include phthalamide, iso-phthalamide, terephthalamide, benzamide, toluamide, p-hydroxybenzamide and m-hydroxybenzamide.

When the compounds containing amino groups and/or amide groups also contain epihalohydrin reactive groups such as hydroxyl groups, carboxyl groups and mercapto groups in addition to the amino groups or amide groups, a part or whole of these epihalohydrin reactive groups may be reacted with epihalohydrin to form epoxy groups.

(ii) Phenol based epoxy resins

Phenol based epoxy resins such as bisphenol-A diglycidyl ether and EPOTOTO YDCN-220 TM (a product of Toto Kasei Co., Ltd.) can be prepared by reacting phenol based compounds with epihalohydrins.

Exemplary suitable phenol based compounds include hydroquinone, catechol, resorcinol, bisphenol-A, bisphenol-F, bisphenol sulfone, brominated bisphenol-A, novolac resin, cresol novolac resin, tetra(hydroxyphenyl)ethane and tri(hydroxyphenyl)ethane.

(iii) Alcohol based epoxy resin

Exemplary suitable resins include trimethylolpropane triglycidyl ether and neopentyl glycol diglycidyl ether. The resins can be prepared by reacting alcohol based compounds with epihalohydrins.

Exemplary alcohol based compounds suitable for use in the process of the invention include polyhydric alcohols such as ethylene glycol, diethylene glycol, triethylene glycol, polyethylene glycol, propylene glycol, dipropylene glycol, polypropylene glycol, 1,4-butanediol, 1,6-hexanediol, neopentyl glycol, dibromoneopentyl glycol, trimethylolpropane, glycerol, pentaerythritol, polycaprolactone, polytetramethylene ether glycol, polybutadiene glycol, hydrogenated bisphenol-A, cyclohexanedimethanol, bisphenol-A.ethyleneoxide adduct and bisphenol-A.propyleneoxide adduct; and polyester polyols prepared from the above polyhydric alcohols and polyatomic carboxylic acids.

(iv) Epoxylated products of unsaturated compounds

Exemplary suitable epoxylated products of unsaturated compounds include cyclopentadienediepoxide, epoxylated soy bean oil, epoxylated polybutadiene, vinylcyclohexenepoxide and ERL-4221 TM, ERL-4234 TM and ERL-4299 TM (products of Union Carbide Corp.).

(v) Glycidyl ester based epoxy resin

Exemplary suitable glycidyl ester based epoxy resins include tetrahydrophthalic acid diglycidyl ester and the like. The resins can be prepared by reacting carboxylic acids with epihalohydrins.

Exemplary carboxylic acids suitable for use in the process of the invention include polyatomic carboxylic acids such as adipic acid, sebacic acid, dodecanedicarboxylic acid, dimer acid, phthalic acid, isophthalic acid, terephthalic acid, tetrahydrophthalic acid, methyltetrahydrophthalic acid, hexahydrophthalic acid, fetic acid, nadic acid, maleic acid, fumaric acid, trimellitic acid, benzenetetracarboxylic acid, butanetetracarboxylic acid, benzophenonetetracarboxylic acid and 5-(2,5-dioxotetrahydrofuryl)-3-methylcyclohexene-1,2-dicarboxylic acid.

(vi) Urethane based epoxy resin

Urethane based epoxy resins can be prepared by reacting the polyhydric alcohols set forth in section (iii) with diisocyanates and glycidols.

Exemplary suitable diisocyanates include tolylene diisocyanate, diphenylmethane-4,4'-diisocyanate, hexamethylene diisocyanate, isophorone diisocyanate, xylylene diisocyanate and naphthalene diisocyanate.

(vii) Alicyclic epoxy resins

Exemplary suitable alicyclic epoxy resins for use in the invention include alicyclic epoxy resins such as 3,4-epoxycyclohexyl-3,4epoxycyclohexanecarboxylate, vinylcyclohexenedioxide, 2-(3,4-epoxycyclohexyl-5,5-spiro-3,4-epoxy)cyclohexane-m-dioxane and bis(3,4-epoxycyclohexyl)adipate.

(viii) Other epoxy resin

Other epoxy resins suitable for use in the process of the invention include tris(epoxypropyl) isocyanurate, glycidyl (meth)acrylate copolymer, diisocyanate compounds of the above epoxy resin and resins modified with dicarboxylic acid, polyhydric phenol and the like.

Epoxy resins obtained by partly or entirely converting the epoxy groups in the epoxy resins set forth in sections (i)–(viii) above to episulfide groups are also suitable for use in the process of the invention.

The above resins may be used singly or in combination as a mixture.

Exemplary polythiol compounds having two or more functional groups suitable for use in the process of the invention include aliphatic polythiols such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, bicyclo[2,2,1]hepta-exo-cis-2,3-dithiol, 1,1-bis(mercaptomethyl)cyclohexane, bis(2-mercaptoethyl)thiomalate, 2-mercaptoethyl-2,3-dimercaptosuccinate, 2,3-dimercapto-1-propanol(2-mercaptoacetate), 2,3-dimercapto-1-propanol(3-mercaptopropionate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl)ether, ethylene glycol bis(2-mercaptoacetate), ethylene glycol bis(3-mercaptopropionate), trimethylolpropane bis(2-mercaptoacetate), trimethylolpropane bis(3-mercaptopropionate), pentaerythritol tetrakis(2-mercaptoacetate) and pentaerythritol tetrakis(3-mercaptopropionate); halogen-substituted compounds such as chlorine-substituted compounds and bromine-substituted compounds of the above aliphatic polythiols; aromatic polythiols such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2-bis(mercaptomethyleneoxy)benzene, 1,3-bis(mercaptomethyleneoxy)benzene, 1,4-bis(mercaptomethyleneoxy)benzene, 1,2-bis(mercaptoethyleneoxy)benzene, 1,3-bis(mercaptoethyleneoxy)benzene, 1,4-bis(mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,-tris(mercaptoethyl)benzene, 1,3,5-tris(mercaptoethyl)benzene, 1,2,3-tris(mercaptomethyleneoxy)benzene, 1,2,4-tris(mercaptomethyleneoxy)benzene, 1,3,5-tris(mercaptomethyleneoxy)benzene, 1,2,3-tris(mercaptoethyleneoxy)benzene, 1,2,4-tris(mercaptoethyleneoxy)benzene, 1,3,5-tris(mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercaptoethyl)benzene, 1,2,3,4-tetrakis(mercaptomethyleneoxy)benzene, 1,2,3,5-tetrakis(mercaptomethyleneoxy)benzene, 1,2,4,5-tetrakis(mercaptomethyleneoxy)benzene, 1,2,3,4-tetrakis(mercaptoethyleneoxy)benzene, 1,2,3,5-tetrakis(mercaptoethyleneoxy)benzene, 1,2,4,5-tetrakis(mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-bis(mercaptomethyl)anthracene, 1,3-di(p-methoxyphenyl)propane-2,2-dithiol, 1,3-diphenylpropane-2,2-dithiol, phenylmethane-1,1-dithiol and 2,4-di(p-mercaptophenyl)pentane; halogen-substituted aromatic polythiols including chlorinated derivatives and brominated derivatives of the above polythiols such as 2,5-dichlorobenzene-1,3-dithiol, 1,3-di(p-chlorophenyl)propane-2,2-dithiol, 3,4,5-tribromo-1,2-dimercaptobenzene and 2,3,4,6-tetrachloro-1,5-bis(mercaptomethyl)benzene; heterocyclic ring containing polythiols such as 2-methylamino-4,6-dithiol-sym-triazine, 2-ethylamino-4,6-dithiol-sym-triazine, 2-amino-4,6-dithiol-sym-triazine, 2-morpholino-4,6-dithiol-sym-triazine, 2-cyclohexylamino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine and 2-thiobutyloxy-4,6-dithiol-sym-triazine; and halogen-substituted compounds including chlorine-substituted derivatives and bromine substituted derivatives of the above heterocyclic ring containing polythiols.

Exemplary polythiol compounds having at least two mercapto groups and containing sulfur atoms in addition to mercapto groups include, for example, aromatic polythiols such as 1,2-bis(mercaptomethylthio)benzene, 1,3-bis(mercaptomethylthio)benzene, 1,4-bis(mercaptomethylthio)benzene, 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, 1,2,3,4-tetrakis(mercaptomethylthio)benzene, 1,2,3,5-tetrakis(mercaptomethylthio)benzene, 1,2,4,5-tetrakis(mercaptomethylthio)benzene, 1,2,3,4-tetrakis(mercaptoethylthio)benzene, 1,2,3,5-tetrakis(mercaptoethylthio)benzene, 1,2,4,5-tetrakis(mercaptoethylthio)benzene and benzene ring alkylated compounds of these aromatic polythiols; aliphatic polythiols such as bis(mercaptomethyl)sulfide, bis(mercaptoethyl) sulfide, bis(mercaptopropyl)sulfide, bis(mercaptomethylthio)methane, bis(2-mercaptoethylthio)methane, bis(3-mercaptopropylthio)methane, 1,2-bis(mercaptomethylthio)ethane, 1,2-bis(2-mercaptoethylthio)ethane, 1,2-bis(3-mercaptopropylthio)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 2,5-dimercapto-1,4-dithian, bis(mercaptomethyl) disulfide, bis(mercaptoethyl)disulfide, bis(mercaptopropyl) disulfide, thioesters of thioglycolic acid and thiopropionic acid esters of the above aliphatic polythiols, hydroxymethylsulfidebis(2-mercaptoacetate), hydroxymethylsulfidebis(3-mercaptopropionate), hydroxyethylsulfidebis(2-mercaptoacetate), hydroxyethylsulfidebis(3-mercaptopropionate), hydroxypropylsulfidebis(2-mercaptoacetate), hydroxypropylsulfidebis(3-mercaptopropionate), hydroxymethyldisulfidebis(2-mercaptoacetate), hydroxymethyldisulfidebis(3-mercaptopropionate), hydroxyethyldisulfidebis(2-mercaptoacetate), hydroxyethyldisulfidebis(3-mercaptopropionate), hydroxypropyldisulfidebis(2-mercaptoacetate), hydroxypropyldisulfidebis(3-mercaptopropionate), 2-mercaptoethyl ether bis(2-mercaptoacetate), 2-mercaptoethyl ether bis(3-mercaptopropionate), 1,4-dithian-2,5-diolbis(2-mercaptoacetate), 1,4-dithian-2,5-diolbis(3-mercaptopropionate), thiodiglycolic acid bis(2-mercaptoethyl ester), thiodipropionic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), dithioglycolic acid bis(2,3-dimercaptopropyl ester) and dithiodipropionic acid bis(2,3-dimercaptopropyl ester); and heterocyclic polythiols such as 3,4-thiophenedithiol, bismuthiol and 2,5-dimercapto-1,3,4-thiadiazol. Halogen-substituted polythiols such as chlorine substituted derivatives and bromine substituted derivatives containing sulfur and mercapto groups in a molecule may also be used. These compounds may be used alone or in combination as a mixture.

The mole ratio of the mercapto groups in the polythiol compounds to the epoxy resin having two or more epoxy groups and/or episulfide groups from about 0.1 to about 2.0 moles, preferably from about 0.2 to about 1.2 moles of mercapto groups per mole of the sum of functional epoxy and episulfide groups.

The internal releasing agents used in the present invention are surface active agents, wax, organosilane compounds, and organofluoro compounds. Among others, surface active agents are used preferably.

The surface active agents used in the present invention are roughly classified into ionic surface active agents and nonionic surface active agents, and the ionic surface active agents are further classified into anionic surface active agents and cationic surface active agents.

Exemplary suitable anionic surface active agents include sulfuric acid esters, sulfonic acid esters and phosphoric acid esters, preferably phosphoric acid esters. Among those, acidic phosphoric acid esters are best. Typical examples of the acidic phosphoric acid ester anionic surface active agents include isopropyl acid phosphate, diisopropyl acid phosphate, butyl acid phosphate, dibutyl acid phosphate, octyl acid phosphate, dioctyl acid phosphate, isodecyl acid phosphate, diisodecyl acid phosphate, dodecanol acid phosphate, and bis(tridecanol) acid phosphate.

The cationic surface active agents are alkyl quaternary ammonium salts that include halogen salts, phosphates, and sulfates of alkyl quaternary ammoniums, and specific examples thereof in the form of chlorides are trimethylcetyl ammonium chloride, trimethylstearyl ammonium chloride, dimethylethylcetyl ammonium chloride, triethyldodecyl ammonium chloride, trioctyldodecyl ammonium chloride, and diethylcyclohexyldodecyl ammonium chloride.

The nonionic surface active agents include polyoxyalkyl fatty acid esters, polyoxyalkyl ethers, compounds having a dimethyl polysiloxane group and a hydroxyalkyl group or a phosphate group, and compounds having a perfluoroalkyl group and a hydroxyalkyl group or a phosphate ester group, and a specific example of the silicon based compound is Q2-120A produced by Dow Chemical Company in U.S.A., and specific examples of the fluorine based compounds are Unidain DS-401 (produced by Daikin Kogyo Co., Ltd.), Unidain DS-403 (produced by Daikin Kogyo Co., Ltd.), F-Top EF-122A (Shin-akita Chemical Co., Ltd.), F-Top EF-126 (Shin-akita Chemical Co., Ltd.), and F-Top EF-301 (Shin-akita Chemical Co., Ltd.).

These surface active agents may be used alone or as a mixture of two or more of them. These surface active agents will be suitably selected depending on the combination of monomers used, the polymerization conditions, the economy or the ease of the handling of the surface active agent. The amount of the surface active agent to be used or the amount of a mixture of the surface active agents to be used is in the range of 1 to 10,000 ppm, for the total amount of the epoxy resin and the polythiol. If the amount of the surface active agent to be used is below 1 ppm, the releasability becomes extremely poor, while if the amount is over 10,000 ppm, the release of the molded product will take place during the cast polymerization, which is not preferable because not only the surface accuracy of the lens will be deteriorated but also the produced lens will unfavorably become turbid and whitish.

Known catalysts for use in the curing of epoxy resin can be employed to accelerate curing in this invention. Exemplary suitable catalysts include tertiary amines, salts of tertiary amines, quaternary ammonium salts, metal salts and various kinds of imidazoles.

Furthermore, in the present invention, various additives may be added to the above raw materials. Exemplary suitable additives include a light stabilizer, an ultraviolet absorber, an anti-oxidant, an oil-soluble dye and a filler.

The present lens is obtained by cast polymerization.

Specifically, the epoxy resin, polythiol having at least two mercapto groups, and an internal releasing agent are mixed. If necessary, a catalyst and other additives are further added, the mixture is deaerated fully, and the uniform monomer/additive mixture is cast into a mold, and is polymerized. The mold comprises a combination of a resin gasket and a metal or glass mold, and the material of the mold is preferably glass in view, for example, of the operability, the productivity, and the surface accuracy of the lens that will be obtained.

Although the polymerization temperature and the polymerization time are selected suitably depending on the type of the monomers, the release agent, the additives such as the catalyst, and the shape and the thickness of the lens to be obtained. Generally, the lens is polymerized and cured at low temperature substantially short of generating optical strain in the lens. Further, after polymerization, the mold may be heated at a temperature more than curing temperature, preferably 100° C. or more to ease releasing the lens.

The thus obtained present polysulfide based resin lens has a high surface accuracy and excellent opticophysical properties, is light in weight, and excellent in impact resistance, and can be suitably used as a lens for glasses and cameras.

If necessary, the present lens can be further improved, for example, the lens can be improved in reflection prevention, can be hardened further, or can be made more fashionable, so that physical treatment or chemical treatment such as surface abrasion, antistatic treatment, hard coat treatment, antireflection coat treatment, dyeing treatment, and light control treatment can be carried out for the lens.

The invention will be further described and clarified by the following examples and comparative examples which are intended to be purely exemplary of the invention.

The performance tests of the resins and lenses, specifically the tests of refractive index, Abbe's number, weatherability, mold releasability and surface accuracy were carried out by the following procedure:

Refractive index and Abbe's number:

Measured at 20° C. with a Pulfrich refractometer.

Weatherability:

A lens resin was set in a weatherometer equipped with a sunshine carbon arc lamp. The lens was taken out after 200 hours and its hue was compared with that of a lens resin before the test. Evaluation was classified into no change (○), slight yellowing (Δ), and yellowing (×).

Appearance:

It was evaluated by visual observation. Mold releasability: When the release was easy after the completion of the polymerization, it was marked with ○, whereas when part or all of the product was not released after the completion of the polymerization, it was marked with ×.

Surface accuracy: It was evaluated by visual, and when it was good, it was marked with ○, whereas when observation was bad, it was marked with ×.

EXAMPLE 1

After mixing 19 g of epoxy resin (epoxy equivalent 190) prepared from bisphenol-A and epichlorohydrin with 12.2 g of pentaerythritoltetrakis(3-mercaptopropionate), 0.08 g of triethylamine and 0.03 g of internal releasing agent (dioctyl acid phosphate) were added and thoroughly mixed.

The resulting mixture was poured into a mold composed of a mold and a gasket, and allowed to stand for 2 hours at room temperature to cure the resin. The lens was easily released from the mold. The lens thus obtained was colorless and transparent, excellent in weatherability, and had a refractive index $n_D^{20}$ of 1.58 and an Abbe's number of 37. The lens had high surface accuracy.

Examples 2 to 12 and Comparative Examples 1 to 2

Following the procedure of Example 1, lenses were prepared in composition ratios shown in Table 1. The results of performance tests are set forth in Table 1.

Comparative Examples 3–10

The same procedure of Example 1 were carried out for preparing lenses except that mold were used under conditions described below and compositions described in Table-2 were used. The results were summarized in Table-2. The descriptions in the mold treatment column in Table-2 also indicated the following conditions.

(1) No treatment ... A glass mold was used without any release treatment.
(2) External release treatment ... External mold releasing agent YSR-6209 ™ (product of Toshiba Silicon Co.) was applied and baked on the inner surface of a glass mold.
(3) Reuse of external release treatment ... The glass mold obtained by the external release treatment was once employed for the polymerization and then used again without any further treatment.
(4) Use of PP mold ... A polypropylene mole was prepared by injection molding and used in place of the glass mold without any surface treatment.

TABLE 1

| | Epoxy resin (g) | Curing agent (g) | Internal releasing agent (ppm) | Refractive index | Abbe's number | Weather-ability | Appearance | Release characteristics | Surface accuracy |
|---|---|---|---|---|---|---|---|---|---|
| Example-2 | BPFDGE[1] (17.4) | PEMP[2] (12.2) | Dibutyl acid phosphate (2000) | 1.60 | 37 | ○ | Colorless and transparent | ○ | ○ |
| Example-3 | TBPADGE[3] (40) | PEMP (12.2) | DS-401 (100) | 1.63 | 34 | ○ | Colorless and transparent | ○ | ○ |
| Example-4 | TBPADGE (40) | PETG[4] (10.8) | EF-301 (200) | 1.64 | 33 | ○ | Colorless and transparent | ○ | ○ |
| Example-5 | BPADGE[5] (19) | PETG (10.8) | Octyl acid phosphate (1500) | 1.60 | 35 | ○ | Colorless and transparent | ○ | ○ |
| Example-6 | BPFDGE (17.4) | PETG (10.8) | Q2-120A (200) | 1.61 | 35 | ○ | Colorless and transparent | ○ | ○ |
| Example-7 | TBPADGE (40) | TMEM[7] (8.8) | trimethyl-cetyl ammonium chloride (2000) | 1.66 | 33 | ○ | Colorless and transparent | ○ | ○ |
| Example-8 | BPFDGE (17.4) | TMEM (8.8) | triethyl-decyl ammonium chloride (2000) | 1.64 | 34 | ○ | Colorless and transparent | ○ | ○ |
| Example-9 | TGPDGE[8] (17.8) | TMEM (8.8) | DS-403 (150) | 1.62 | 33 | ○ | Colorless and transparent | ○ | ○ |
| Example-10 | TGPDGE (17.8) | PETG (10.8) | EF-122A (200) | 1.63 | 31 | ○ | Colorless and transparent | ○ | ○ |
| Example-11 | Vinylcyclohexene diepoxide (20) | TMEM (8.8) | Dibutyl acid phosphate (2000) | 1.64 | 44 | ○ | Colorless and transparent | ○ | ○ |
| Example-12 | Vinylcylcohexene diepoxide (20) | PETG (10.8) | Dibutyl acid phosphate (2000) | 1.58 | 52 | ○ | Colorless and transparent | ○ | ○ |
| Comp. Example-1 | TBPADGE (40) | HHPA[8] | Dibutyl acid phosphate (2000) | 1.54 | | ○ | Colorless and transparent | ○ | ○ |
| Comp. Example-2 | 3,4-Epoxycyclohexylmethyl-3,4-epoxycyclohexane | Tetrabromo phtharic acid anhydride | Dibutyl acid phosphate (2000) | 1.59 | | ○ | Colorless and transparent | ○ | ○ |

TABLE 1-continued

| | Epoxy resin (g) | Curing agent (g) | Internal releasing agent (ppm) | Refractive index | Abbe's number | Weather-ability | Appear-ance | Release character-istics | Surface accuracy |
|---|---|---|---|---|---|---|---|---|---|
| | carboxylate (30) | (70) | | | | | | | |

[1] Bisphenol-F diglycidyl ether: Epoxy equivalent 174
[2] Pentaerythritoltetrakis(mercaptopropionate)
[3] Tetrabromobisphenol-A diglycidyl ether: Epoxy equivalent 400
[4] Pentaerythritoltetrakis(thioglycolate)
[5] Bisphenol-A diglycidyl ether: Epoxy equivalent 190
[6] Thiodiphenol diglycidyl ether: Epoxy equivalent 178
[7] Tetrakis(2-mercaptoethylthiomethyl)methane
[8] Hexahydrophthalic acid
[9] Vinylcyclohexene diepoxide: Epoxy equivalent 75

TABLE 2

| | Epoxy resin (g) | Curing agent (g) | Mold treatment | Refractive index | Abbe's number | Weather-ability | Appear-ance | Release character-istic | Surface accuracy |
|---|---|---|---|---|---|---|---|---|---|
| Comp. Example-3 | Vinylcyclo-hexene epoxide (20) | TMEM (31.4) | No treatment | — | — | — | — | x | — |
| Comp. Example-4 | Vinylcyclo-hexene epoxide (20) | TMEM (31.4) | External release treatment (YSR-6209) | 1.64 | 44 | ○ | Colorless transparent | ○ | x |
| Comp. Example-5 | Vinylcyclo-hexene epoxide (20) | TMEM (31.4) | Reuse of External release treatment (mold used in Comp. Ex. 4) | — | — | — | — | x | — |
| Comp. Example-6 | Vinylcyclo-hexene epoxide (20) | TMEM (31.4) | Use of PP mold | 1.64 | 44 | ○ | Colorless transparent | ○ | x |
| Comp. Example-7 | BPFDGE (17.4) | PEMP (12.2) | No treatment | — | — | — | — | x | — |
| Comp. Example-8 | BPFDGE (17.4) | PEMP (12.2) | External release treatment (MS-181) | 1.60 | 37 | ○ | Colorless transparent | ○ | x |
| Comp. Example-9 | BPFDGE (17.4) | PEMP (12.2) | Reuse of Extrenal release treatment (mold used in Comp. Ex. 8) | — | — | — | — | x | — |
| Comp. Example-10 | BPFDGE (17.4) | PEMP (12.2) | Use of PP mold | 1.60 | 37 | ○ | Colorless transparent | ○ | x |

What is claimed is:

1. A polysulfide based resin lens having a refractive index of 1.58 to 1.66, comprising forming a mixture consisting essentially of:
   a) at least one epoxy resin, which has at least two epoxy groups selected from the group consisting of (i) amine based epoxy resins, (ii) phenol based epoxy resins, (iii) alcohol based epoxy resins, (iv) epoxylated products of unsaturated compounds, (v) glycidyl ester based epoxy resins, (vi) urethane based epoxy resins, (vii) alicyclic epoxy resins, and (viii) heterocyclic ring-containing epoxy resins;
   b) at least one polythiol compound which has at least two mercapto groups, selected from the group consisting of (i) aliphatic polythiols, (ii) aromatic polythiols, (iii) heterocyclic ring-containing polythiols, (iv) aliphatic polythiols containing sulfur atoms in addition to mercapto groups, (v) aromatic polythiols containing sulfur atoms in addition to mercapto groups and (vi) heterocyclic ring-containing polythiols containing sulfur atoms in addition to mercapto groups, the mole ratio of the mercapto groups in the polythiol compounds to the epoxy resin being from 0.2 to 1.2 moles of mercapto groups per mole of the sum of functional epoxy groups; and
   c) at least one internal releasing agent selected from the group consisting of phosphoric acid esters, alkyl quaternary ammonium salts, silicon based nonionic surface active agents and fluorine based nonionic surface active agents, at a concentration of 1 to 10,000 ppm per the total weight of the epoxy resin and the polythiol compound, and then cast-polymerizing said mixture in a mold, and releasing a lens from the mold.

2. The lens of claim 1 wherein the fluorine based nonionic surface active agent is a compound having a perfluoroalkyl group and having a hydroxyalkyl group or phosphoric acid ester group.

3. The lens of claim 1 wherein the silicon based nonionic surface active agent is a compound having a dimethylpolysiloxane group and having a hydroxyalkyl group or phosphoric acid ester group.

4. The lens of claim 1 wherein said phosphoric acid ester is an acidic phosphoric acid ester.

5. The lens of claim 1 wherein said acidic phosphoric acid ester is at least one compound selected from isopropyl acid phosphate, diisopropyl acid phosphate, butyl acid phosphate, dibutyl acid phosphate, octyl acid phosphate, dioctyl acid phosphate, isodecyl acid phosphate, diisodecyl acid phosphate, tridecanol acid phosphate and bis(tridecanol) acid phosphate.

6. The lens of claim 1 wherein said quaternary ammonium salt is one or more compounds selected from the group consisting of halogen salts, phosphates of trimethylcetyl ammonium, trimethylstearyl ammonium, dimethylethylcetyl ammonium, triethyldodecyl ammonium, trioctylmethyl ammonium and diethylcyclohexyldodecyl ammonium.

* * * * *